United States Patent
Mais et al.

(10) Patent No.: US 6,562,970 B1
(45) Date of Patent: May 13, 2003

(54) METHOD FOR PRODUCING 4-CHLORO-6-HYDROXYPYRIMIDINE

(75) Inventors: Franz-Josef Mais, Düsseldorf (DE); Günther Cramm, Leverkusen (DE); Alexander Klausener, Pulheim (DE); Guido Steffan, Odenthal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 80 days.

(21) Appl. No.: 10/019,211

(22) PCT Filed: Jun. 13, 2000

(86) PCT No.: PCT/EP00/05406

§ 371 (c)(1),
(2), (4) Date: Dec. 20, 2001

(87) PCT Pub. No.: WO01/00593

PCT Pub. Date: Jan. 4, 2001

(30) Foreign Application Priority Data

Jun. 26, 1999 (DE) .......................................... 199 29 351

(51) Int. Cl.$^7$ .............................................. C07D 239/02
(52) U.S. Cl. ...................................... 544/319; 544/319
(58) Field of Search .......................................... 544/319

(56) References Cited

PUBLICATIONS

J. Med. Chem. 7, 5, Jan. 8, 1964, pp. 1–10, Charles Heidelberger, David G. Parsons and David C. Remy, Syntheses of 5–Trifluoromethyluracil and 5–Trifluoromethyl–2'–decoxyuridine .

*Desmond J. Brown: "Pyrimidine Reactions. XSVII." Australian Journal of Chemistry, vol. 31, No. 2, Feb. 1978, pp. 1391–1395, XP000960999 Australia.

*Primary Examiner*—John M. Ford
(74) *Attorney, Agent, or Firm*—Joseph C. Gil; John E. Mrozinski; Diderico van Eyl

(57) ABSTRACT

The present invention relates to a process for preparing 4-chloro-6-hydroxypyrimidine from 4-chloro-6-methoxypyrimidine.

10 Claims, No Drawings

METHOD FOR PRODUCING 4-CHLORO-6-HYDROXYPYRIMIDINE

The present invention relates to a process for preparing 4-chloro-6-hydroxypyrimidine from 4-chloro-6-methoxypyrimidine. 4-Chloro-6-hydroxypyrimidine is a valuable intermediate for preparing crop protection agents, with the first stage of further processing frequently comprising a conversion of 4-chloro-6-hydroxypyrimidine into 4,6-dichloropyrimidine.

Various methods for synthesizing 4-chloro-6-hydroxypyrimidine have been disclosed. For example, J. Chem. Soc. (1961), 1298 describes the hydrolysis of 4,6-dichloropyrimidine with aqueous hydrochloric acid.

According to J. Med. Chem. 7, 5 (1964) a methylthio group is eliminated from 4-chloro-6-hydroxy-2-methylthiopyrimidine or a diazotizing hydroxylation of 4-amino-6-chloropyrimidine is carried out.

Furthermore, J. Org. Chem. USSR (English translation) 2, 230 (1966) describes the alkaline hydrolysis of a compound of the type Het-O—NH—CO—O—$C_2H_5$ to the compound Het-OH where Het-OH is said to represent 4-chloro-6-hydroxypyrimidine.

The disadvantages of these processes are that they start from the desired product of further processing, that they require starting materials which are difficult to obtain, that they can be carried out only in a time-consuming and complicated manner and/or that they produce sulfur-containing waste products which can be disposed of only in a complicated manner.

Furthermore, Helv. Chim. Acta 42, 1317 (1959) describes the hydrolysis of 4-chloro-6-methoxypyrimidine to 4-chloro-6-hydroxypyrimidine using aqueous hydrochloric acid as reagent.

The disadvantage of this process is that the product can be isolated only by a time-consuming workup and, for the desired further processing to 4,6-dichloropyrimidine, it must be carefully dried.

A process for preparing 4-chloro-6-hydroxypyrimidine which is characterized in that 4-chloro-6-methoxypyrimidine is reacted with hydrogen halide has now been found.

Examples of a suitable hydrogen halide are HCl, HBr and HI. HCl and HBr are preferred, and HCl is particularly preferred. The use of mixtures of hydrogen halides is also possible. The hydrogen halides can be employed for example as such or mixed with a solvent, for example mixed with one of the solvents described below. The hydrogen halide is generally substantially anhydrous, that is to say it contains, for example, less than 1 mol %, preferably less than 0.1 mol %, of water.

A further possibility is to generate the hydrogen halides to be employed in situ from a halogen compound, for example an inorganic or organic acid halide, and a protic compound, for example water, an alcohol or an inorganic or organic acid. In this case, preferably only as much of the protic compound, in particular water, is employed as is used to form hydrogen halide.

It is possible to employ per mole of 4-chloro-6-methoxypyrimidine for example 1 to 30 mol, preferably 2 to 15 mol, of hydrogen halide. An excess of hydrogen halide is advantageous especially when unreacted hydrogen halide escapes during the reaction.

Solvents suitable in principle are those which do not interfere with the reaction of the invention, for example aliphatic solvents such as alkanes, cycloalkanes, halogenoalkanes and aliphatic ethers, aromatic solvents such as benzene, toluene, xylenes, halogenobenzenes, halogenotoluenes and benzotrifluorides, alcohols with 1–4 C atoms such as ethanol and isopropanol, nitriles such as acetonitrile and benzonitrile, nitrogen-containing solvents such as dimethylformamide, dimethylacetamide, cyclic ureas and lactams and ethers such as alkyl ethers, aryl ethers, alkyl aryl ethers and polyethers. Toluene, xylenes, dimethylformamide, acetonitrile, dichlorobenzenes or chlorotoluenes are preferably employed.

Special drying of the solvents is unnecessary. They can be employed with the water content normally present in technical grades. It is possible where appropriate to add small amounts of water or alcohols as catalysts to the process of the invention, for example 0.1 to 1.0 mol % based on 4-chloro-6-methoxypyrimidine employed. However, such an addition of catalyst can also be dispensed with.

The process of the invention can be carried out, for example, at temperatures in the range 0 to 200° C. 40 to 180° C. are preferred, and 60 to 160° C. are particularly preferred.

The pressure in the process of the invention is not critical, possible examples being 0.1 to 20 bar. 0.5 to 3 bar are preferred. Atmospheric pressure is particularly preferred.

A further possibility is not to isolate 4-chloro-6-hydroxypyrimidine but to meter a chlorinating agent, for example phosphorus oxychloride or phosgene, directly into the reaction mixture after the end of the reaction of the invention and thus convert it into 4,6-dichloropyrimidine. The precondition for this procedure is that the process of the invention is carried out in solvents which do not react in an unwanted manner with the chlorinating agent.

The process of the invention can be carried out in various embodiments, for example batchwise, semicontinuously, continuously or semibatchwise. Examples of possible procedures are as follows: dry hydrogen halide is passed at the desired reaction temperature into 4-chloro-6-methoxypyrimidine in a solvent.

With suitable choice of the solvent, for example of the preferred solvents indicated above, it is possible after the reaction of 4-chloro-6-methoxypyrimidine is substantial or complete for the reaction mixture to be brought to a temperature for example in the range 5 to 30° C., and for the precipitated product to be filtered off with suction.

Another possibility is to meter in hydrogen halide which is dissolved in one of the abovementioned solvents.

A further possibility is to meter 4-chloro-6-methoxypyrimidine into hydrogen halide in one of the abovementioned solvents and to stir at room temperature.

Working up is also possible by distillation. Besides these, other reaction procedures and workups are also possible.

The process of the invention makes it possible to prepare 4-chloro-6-hydroxypyrimidine in an exceptionally simple manner. For example, the conversion can be brought about by simply passing hydrogen halide into a solution of 4-chloro-6-methoxypyrimidine. It is particularly advantageous that the eliminated methyl group results in the form of methyl halide which escapes in the form of a gas from the system. This is particularly the case when hydrogen chloride is used. A further great advantage is that, if the solvent is suitably chosen, the 4-chloro-6-hydroxypyrimidine which is formed precipitates and can be isolated in a simple manner, for example by filtration.

EXAMPLES

Example 1

100 parts by weight of xylene (mixture of isomers) and 30 parts by weight of 4-chloro-6-methoxypyrimidine were introduced into a stirred vessel. Then, while stirring at 100° C., gaseous hydrogen chloride (technical grade) was passed in at a rate of 20 parts by weight per hour. After 5 hours, the hydrogen chloride feed was stopped, and the reaction mixture was cooled to room temperature and analyzed by HPLC. A content of 2.7% 4-chloro-6-methoxypyrimidine and 18.9% 4-chloro-6-hydroxypyrimidine was found. The final weight of the reaction mixture was 125.5 parts by weight, which corresponds to an amount of 11.3% of the 4-chloro-6-methoxypyrimidine starting material and a 4-chloro-6-hydroxypyrimdine yield of 87.4% of theory.

Example 2

The procedure was as in Example 1 but 100 parts by weight of dimethylformamide were introduced in place of 100 parts by weight of xylene. After the passing in of hydrogen chloride and the cooling to room temperature, the final weight was 149.5 parts by weight. The HPLC content was 18.0% 4-chloro-6-hydroxypyrimidine. Only traces of 4-chloro-6-methoxypyrimidine were now detectable. This corresponds to an HPLC yield of 99.1%.

The reaction mixture was subsequently evaporated in vacuo (15 mbar) at a bottom temperature of 120° C. A clear colorless distillate of 116.2 parts by weight and a residue of 32.6 parts by weight were obtained (loss: 0.7 part by weight). HPLC analysis of the residue showed a content of 82.0% 4-chloro-6-hydroxypyrimidine, corresponding to a yield of 98.5% of theory.

Example 3

240 parts by weight of acetonitrile (technical grade), 80 parts by weight of 4-chloro-6-methoxypyrimidine and 8 parts by weight of dimethylformamide were introduced into a stirred vessel and heated to reflux. At this temperature, 150 parts by weight of gaseous hydrogen chloride (technical grade) were passed in at a constant rate over the course of 5.5 hours. The mixture was subsequently cooled to 20° C., filtered with suction and washed with 80 parts by weight of acetonitrile. Drying resulted in 85.2 parts by weight of an almost colorless powder. The HPLC content was 74.7% 4-chloro-6-hydroxypyrimidine, corresponding to a yield of 4-chloro-6-hydroxypyrimidine HCl salt of 88.1% of theory. The combined mother liquors and washings were evaporated in a rotary evaporator and analyzed by HPLC. 4-Chloro-6-hydroxypyrimidine was present in an amount of 2.6% of theory and 4-chloro-6-methoxypyrimidine was present in an amount of 0.58% of the starting material.

Example 4

100 parts by weight of acetonitrile, 55 parts by weight of thionyl chloride and 14.5 parts by weight of 4-chloro-6-methoxypyrimidine were introduced into a stirred vessel. The mixture was stirred at 80° C. and 3.6 parts by weight of water were metered in at a constant rate over the course of 3 hours. The water reacted immediately with the thionyl chloride to form hydrogen chloride and sulfur dioxide. The mixture was then stirred at 80° C. for 1 hour. After cooling to room temperature, a final weight of 140.4 parts by weight was obtained. The HPLC content was 8.24% 4-chloro-6-hydroxypyrimidine. This corresponded to a yield of 88.7% of theory.

Example 5

100 parts by weight of o-dichlorobenzene and 10 parts by weight of 4-chloro-6-methoxypyrimidine were introduced into a stirred vessel and heated to 150° C. with stirring. At this temperature, 15 parts by weight of gaseous hydrogen chloride (technical grade) were passed in at a constant rate over the course of 1.5 hours. The final weight after cooling was 98.7 parts by weight. The HPLC content was 9.23% 4-chloro-6-methoxypyrimidine, corresponding to a yield of 88.3% of theory. 4-Chloro-6-methoxypyrimidine was no longer detectable in the reaction mixture.

What is claimed is:

1. A process for preparing 4-chloro-6-hydroxypyrimidine comprising reacting 4-chloro-6-methoxypyrimidine and a hydrogen halide.

2. The process according to claim 1, wherein the hydrogen halide is selected from the group consisting of HCl, HBr, HI, and mixtures thereof.

3. The process according to claim 1, wherein the hydrogen halide is present in an amount ranging from 1 to 30 mol, per mole of 4-chloro-6-methoxypyrimidine.

4. The process according to claim 1, wherein the process is carried out in the presence of aliphatic solvents, aromatic solvents, nitrites, nitrogen-containing solvents or ethers.

5. The process according to claim 1, wherein the process is carried out at a temperature ranging from 0 to 200° C.

6. The process according to claim 1, wherein the process is carried out under a pressure ranging from 0.1 to 20 bar.

7. The process according to claim 1, wherein the process is carried out batchwise, semicontinuously, continuously or semibatchwise.

8. The process according to claim 1, wherein the 4-chloro-6-methoxypyrimidine is introduced into a solvent and the 4-chloro 6-methoxypyrimidine then reacts with the hydrogen halide.

9. The process according to claim 8, wherein the process is carried out in the presence of toluene, xylenes, dimethylformamide, acetonitrile, chlorobenzene, dichlorobenzenes or chlorotoluenes and, after the reaction of 4-chloro-6-methoxypyrimidine is substantially carried out or completed, the reaction mixture is brought to a temperature in the range from 5 to 30° C. and the precipitated product is finally filtered off with suction.

10. The process according to claim 1, wherein the hydrogen halide is generated in situ from a halogen compound and a protic compound.

* * * * *